US007470313B2

(12) United States Patent
Lenox et al.

(10) Patent No.: US 7,470,313 B2
(45) Date of Patent: Dec. 30, 2008

(54) AMINO ACID-SOLUBILIZED BORATE, SILICATE AND ZINC COMPOSITIONS AND METHODS FOR TREATING WOOD PRODUCTS

(75) Inventors: Jason D. Lenox, Boyertown, PA (US); Neil T. Miller, King of Prussia, PA (US); Matthew Rossi, Springfield, PA (US)

(73) Assignees: PQ Corporation, Berwyn, PA (US); U.S. Borax Inc., Greenwood Village, CO (US)

( * ) Notice: Subject to any disclaimer, the term of this patent is extended or adjusted under 35 U.S.C. 154(b) by 0 days.

(21) Appl. No.: 11/547,376

(22) PCT Filed: Mar. 31, 2005

(86) PCT No.: PCT/US2005/010893

§ 371 (c)(1),
(2), (4) Date: Oct. 4, 2007

(87) PCT Pub. No.: WO2005/094586

PCT Pub. Date: Oct. 13, 2005

(65) Prior Publication Data

US 2008/0069978 A1 Mar. 20, 2008

Related U.S. Application Data

(60) Provisional application No. 60/559,484, filed on Apr. 3, 2004.

(51) Int. Cl.
*A01N 59/14* (2006.01)
*A01N 59/16* (2006.01)
*A01N 31/00* (2006.01)
*B05D 7/06* (2006.01)
*B27K 3/20* (2006.01)
*B27K 3/22* (2006.01)

(52) U.S. Cl. .................. 106/18.3; 106/15.05; 106/18.3; 424/405; 424/641; 424/DIG. 11; 427/297; 427/397; 427/397.8; 427/440; 428/537.1; 428/921; 514/557

(58) Field of Classification Search .............. 106/15.05, 106/18.12, 18.3; 424/405, 641, DIG. 11; 427/297, 397, 397.8, 440; 428/537.1, 921; 514/557
See application file for complete search history.

(56) References Cited

U.S. PATENT DOCUMENTS

| 2,194,827 | A | * | 3/1940 | Gordon ....................... 424/601 |
| 3,306,765 | A | | 2/1967 | Du Fresne et al. |
| 3,974,318 | A | * | 8/1976 | Lilla ............................ 442/63 |
| 4,656,060 | A | * | 4/1987 | Krzyzewski ................ 427/397 |
| 4,731,265 | A | | 3/1988 | Hirao et al. |
| 4,857,365 | A | | 8/1989 | Hirao et al. |
| 5,207,823 | A | * | 5/1993 | Shiozawa ................ 106/18.13 |
| 5,478,598 | A | * | 12/1995 | Shiozawa .................... 427/297 |
| 6,146,766 | A | | 11/2000 | Slimak et al. |
| 6,303,234 | B1 | | 10/2001 | Slimak et al. |
| 6,896,908 | B2 | * | 5/2005 | Lloyd et al. .................. 424/635 |
| 2001/0002282 | A1 | | 5/2001 | Grantham et al. |
| 2003/0104135 | A1 | | 6/2003 | Granthan et al. |
| 2004/0166246 | A1 | | 8/2004 | Holcomb |
| 2008/0124478 | A1 | | 5/2008 | Hu et al. |
| 2008/0166481 | A1 | | 7/2008 | Hu et al. |

FOREIGN PATENT DOCUMENTS

| JP | 56-25363 A | 6/1980 |
| JP | 06336408 A2 | 12/1994 |
| JP | 1995251403 A | 10/1995 |
| JP | 2000-108108 A * | 4/2000 |
| WO | WO 01/70472 A1 | 9/2001 |
| WO | WO 2005/096821 | 10/2005 |
| WO | WO 2005/096822 | 10/2005 |

OTHER PUBLICATIONS

Furuno, T. et al., "Combinations of wood and silicate Part 6. biological resistances of wood-mineral composites using water glass-boron compound system", Wood Science and Technology, 32 91998) pp. 161-170, Springer-Verlag 1998, [no month].

Dev, Indra et al., "Terminate resistance and permanency tests on zinc-borate - an environmental friendly preservative", J. Timb. Dev. Assoc. (Inda), vol. XLIII, No. 2, Apr. 1997.

\* cited by examiner

*Primary Examiner*—Anthony J Green
(74) *Attorney, Agent, or Firm*—Kurt R. Ganderup

(57) ABSTRACT

Compositions and methods are provided for treating products containing wood fibers to provide protection against wood destroying organisms and fire, and resistance against leaching of the preservative from the wood fibers by water in exposed environments such as exterior applications. The methods involve applying to a substrate an aqueous preservative composition containing a boron compound, a source of zinc, an aqueous silicate, a source of alkalinity, and an amino acid. The compositions may be applied by vacuum and/or pressure treatment or dip treatment under atmospheric pressure.

30 Claims, No Drawings

ABSTRACT

AMINO ACID-SOLUBILIZED BORATE, SILICATE AND ZINC COMPOSITIONS AND METHODS FOR TREATING WOOD PRODUCTS

This application claims the benefit of U.S. Provisional Application No. 60/559,484, filed on Apr. 3, 2004, the entire contents of which are incorporated herein by reference.

FIELD OF THE INVENTION

This invention relates to the preservation of wood and more particularly, the invention provides compositions and methods for treating wood and wood products to provide leach-resistant protection against insect and fungal attack, as well as resistance to fire.

BACKGROUND OF THE INVENTION

Inorganic borate compounds have been used as wood preservatives for many years for protection against termites and other wood destroying insects, as well as fungal decay. Soluble borates such as borax, boric acid and disodium octaborate tetrahydrate are well known preservatives in aqueous-based systems for treating solid wood for use in protected environments. However, due to their water solubility they are readily leached from treated wood in exposed environments such as exterior and ground contact applications.

Copper chrome arsenate (CCA) is a leach-resistant wood preservative that has been used for many years to treat solid wood for use in exterior applications. However, due to environmental health and safety issues, and toxicity concerns relating to the constituent metals, particularly arsenic, CCA has come under increasing regulatory pressure and is being phased out of use in many areas. Even compositions containing copper without chromium or arsenic are coming into disfavor for environmental reasons, and thus it is desirable to reduce or eliminate copper content as well.

Solid zinc borate has proven very useful as a preservative for wood composites, where it is added as a solid material during manufacture of the composites. The inherent low solubility of zinc borate makes it resistant to leaching, even in high moisture environments. However, in view of its low solubility, it is not so easy to treat solid lumber with zinc borate. Dev et al. (*J. Timb. Dev. Assoc.*, 1997) describes a two-stage process for treating solid wood with zinc borate which involved impregnating the wood with solutions of borax and zinc in two separate steps. Ammonia-based solutions have been proposed to solubilize metals such as zinc and copper in an attempt to fix borates in wood. U.S. Pat. No. 2,194,827 (Gordon) discloses an aqueous ammonia solution of copper, zinc and borate salts for the treatment of wood.

U.S. Pat. No. 3,974,318 to Lilla discloses a method for fire retarding and preserving wood products, paper, cardboard, boxboard, cloth and other porous materials having a plurality of internal voids, in which a water soluble silicate composition is applied to the porous materials, penetrating into the voids, followed by drying the material. Thereafter, a water soluble metallic salt composition is applied, also penetrating into the voids and reacting in situ to form a water insoluble metallic silicate with a high degree of water of hydration disposed throughout the voids.

Shiozawa (U.S. Pat. No. 5,478,598) discloses a wood preservative composition that includes a first solution having: a copper compound selected from the group consisting of copper borate, copper hydroxide, copper acetate, copper chloride, and copper sulfate; a zinc compound selected from the group consisting of zinc borate, zinc acetate, zinc hydroxide, zinc oxide, zinc chloride, and zinc sulfate; and/or a boron compound selected from the group consisting of boric acid and borax; sodium silicate, and a second solution having rare earth chloride or alkaline earth chloride. The inventor states that the inventive composition can be retained in the wood while the leaching thereof out of the wood is prevented.

SUMMARY OF THE INVENTION

In one aspect, the invention provides an aqueous preservative composition comprising a source of zinc selected from the group consisting of zinc oxide and soluble zinc salts; a source of borate selected from the group consisting of zinc borate, boric acid, boric oxide and water soluble borate salts; an amino acid; an alkali metal silicate; a source of alkalinity; and water; wherein the composition comprises at least 50 wt % water.

In another aspect, the invention provides an aqueous preservative composition consisting essentially of a source of zinc selected from the group consisting of zinc oxide and soluble zinc salts; a source of borate selected from the group consisting of zinc borate, boric acid, boric oxide and water soluble borate salts; an amino acid; an alkali metal silicate; a source of alkalinity; and water; wherein the composition comprises at least 50 wt % water.

In yet another aspect, the invention provides a method of making an aqueous preservative composition, the method comprising the steps of: (a) dissolving a source of zinc in an aqueous amino acid-containing solution comprising a source of alkalinity to produce an aqueous zinc solution; (b) adding to the aqueous zinc solution a source of borate selected from the group consisting of zinc borate, boric acid, boric oxide and water soluble borate salts; (c) mixing until essentially all solids are dissolved; and (d) adding to the mixture produced in step (c) an alkali metal silicate.

In still another aspect, the invention provides a method for preserving an article comprising wood fibers, the method comprising the steps of:

(a) applying to the article an aqueous preservative composition prepared by combining ingredients comprising:

i) a source of zinc selected from the group consisting of zinc oxide and soluble zinc salts;

ii) a source of borate selected from the group consisting of zinc borate, boric acid, boric oxide and water soluble borate salts;

iii) an amino acid;

iv) a source of alkalinity;

v) an alkali metal silicate; and vi) water such that the aqueous preservative composition penetrates into the wood fibers, wherein the composition is essentially copper-free and comprises at least 50 wt % of water; and (b) drying the wood fibers;

such that there is deposited therein a bioeffective amount of a residual component comprising zinc, boron, and silicon.

In a further aspect, the invention provides an article comprising wood fibers comprising a residual component comprising zinc, boron, and silicon, prepared by treating the wood fibers according to the method set forth in the immediately preceding paragraph.

In a still further aspect, the invention provides a method for treating a substrate comprising wood fibers to provide resistance to flame spread, the method comprising the steps of:

(a) applying to the article an aqueous preservative composition prepared by combining ingredients comprising:

i) a source of zinc selected from the group consisting of zinc oxide and soluble zinc salts;

ii) a source of borate selected from the group consisting of zinc borate, boric acid, boric oxide and water soluble borate salts;
iii) an amino acid;
iv) a source of alkalinity;
v) an alkali metal silicate; and
vi) water such that the aqueous preservative composition penetrates into the wood fibers, wherein the composition is essentially copper-free and comprises at least 50 wt % of water; and (b) drying the wood fibers;

such that there is deposited therein a flame retardant amount of a residual component comprising zinc, boron, and silicon.

DETAILED DESCRIPTION OF THE INVENTION

The invention provides a system and method for preservative treatment of items comprising wood fibers. The method involves first treating the item with an aqueous preservative composition comprising zinc, borate, and silicate, also comprising an amino acid and a source of alkalinity. The preservative compositions are useful in the treatment of such items to provide borate leach-resistant protection against wood destroying organisms such as termites or other wood destroying insects, and decay fungi. They may also provide other benefits to items with which they are treated, including providing resistance to fire. The compositions may contain copper, or may be essentially copper free, by which it is meant that copper, if present at all, is present only as an impurity in the compositions of this invention, and is not purposely added. In any case, compositions that are "essentially copper free" contain less than 0.1% copper by weight.

As used herein, the term "residual component" refers to a material comprising zinc, boron, and silicon that remains in an article after being contacted with a composition according to the invention. It will be understood that the residual component may vary in composition according to the exact ratio and identity of the zinc, boron, and silicate sources used in the treatment compositions, as well as the amount and type of other materials that may be included in the compositions.

As used herein, the term "bioeffective amount" as applied to a residual component means an amount of material sufficient to reduce or eliminate attack or residence on a treated article by one or both of an insect and a fungus that causes rot. Such reduction or elimination may be by any means, including but not limited to repelling, killing, and prevention of growth on or in the treated article.

As used herein, the term "flame retardant amount" as applied to a residual component means an amount of material sufficient to reduce or eliminate flame spread on a treated article.

As used herein, the term "essentially chloride ion free" means that none of the ingredients comprises chloride ion, other than as an impurity. In any case, a composition that is "essentially chloride free" contains less than 0.1% chlorine by weight.

As used herein, the term "sodium borate" means one or more of disodium octaborate tetrahydrate, sodium tetraborate decahydrate (borax), sodium tetraborate pentahydrate, sodium tetraborate (anhydrous borax), sodium metaborate, sodium pentaborate, and mixtures of any of these. The term "water soluble borate salt" means any sodium borate, any analogous potassium borate, any analogous ammonium borate, or mixtures of any of these.

References to amounts of amino acid in a composition refer to the amount of that material calculated as its unbound form, although it will be understood that equilibrium processes may cause at least some of the compound to be in the form of a salt or other chemical species.

The preferred concentrations of zinc, boron, and amino acid for the aqueous preservative composition are between about 0.1 and 1 percent by weight boron (B), between about 0.2 and 2.5 percent by weight zinc (Zn) and between about 1 and 5 percent by weight amino acid. The preferred zinc to boron (Zn:B) mole ratio in the aqueous preservative composition is at least 0.4:1, typically at least 1:1, and more typically at least 1.5:1. The preferred ratio is at most 5:1, typically at most 3:1, and more typically at most 2:1. The preferred amino acid to zinc mole ratio in the aqueous preservative composition is in the range of about 7:1 to about 33:1. It has been found that choice of Zn:B and amino acid:zinc ratios within the ranges specified above, combined with the absolute concentration ranges set forth above, provides compositions having both good shelf life stability against gelling and precipitation and high resistance to leach-out of borate in items treated with the compositions. The compositions typically contain at least 50 wt % water, but compositions having a higher concentration of active ingredients and a less than 50% water content may be used according to the invention. Such compositions may, for example, be kept as concentrates and diluted as needed prior to application.

The aqueous preservative composition also comprises a soluble silicate compound. Suitable nonlimiting examples of soluble silicate compounds include alkali metal silicates and ammonium silicates. A liquid or water-soluble solid form of silicate may be used. Preferred silicates include the alkali metal silicates, e.g. sodium or potassium silicate, in liquid form. Preferably the alkali metal silicate is sodium silicate, and more preferably it is sodium silicate having an $SiO_2$:$Na_2O$ weight ratio greater than 3:1. Most preferably the sodium silicate has a silicate to sodium ($SiO_2$:$Na_2O$) weight ratio of about 3.22:1. Such materials are commercially available under the trade names N®Silicate and N®Clear, sold by the PQ Corporation of Valley Forge, Pa. The concentration of the silicate (measured as $SiO_2$) in the aqueous preservative composition may be between about 0.1% and 1%, according to the invention.

Higher molar Zn/B ratios reduce leaching of borate from substrate, provided that the resulting compositions do not suffer significant precipitation or gelation. Upper limits of Zn/B may however be imposed by practical considerations regarding stability of the formulation, and/or by precipitation or gelling reactions that occur due to the interaction of high concentrations of zinc with other ingredients.

Zinc Sources

Suitable sources of zinc for use according to the invention may be provided in the form of various zinc compounds including zinc oxide, zinc chloride, zinc acetate, zinc sulfate, and other water-soluble zinc salts. Other zinc salts such as zinc naphthenate, zinc acetylacetonate, zinc gluconate, and zinc complexes with chelating agents such as EDTA may also be used according to the invention. Alternatively, zinc borate may be used. In some embodiments of the invention, zinc chloride is a preferred source of zinc. In other embodiments, for example where it is desired to reduce the chloride ion content in the composition for purposes such as prevention of corrosion, zinc acetate or zinc sulfate may be preferred. Zinc serves to reduce the tendency of borate to leach from the wood upon exposure to water after it has been treated, possibly by formation of a zinc borate precipitate which is not readily soluble in water. Zinc may also contribute to the biocidal properties of the preservative compositions of the present invention. The amino acid and the source of alkalinity aid the dissolution of zinc in the aqueous preservative composition.

Source of Borate

Suitable sources of borate for use according to the invention include boric acid and the water-soluble salts thereof. Alternatively, zinc borate may be used. Preferred sources of borates include the sodium borates, such as disodium octaborate tetrahydrate (commercially available as TIM-BOR® industrial wood preservative manufactured by U.S. Borax Inc., Valencia, Calif.), sodium tetraborate decahydrate (borax), sodium tetraborate pentahydrate, anhydrous sodium tetraborate, sodium metaborate and sodium pentaborate, as well as other alkali metal borates and ammonium borates such as potassium tetraborate, potassium metaborate and ammonium pentaborate. Boric acid and boron oxide may also be used.

Amino Acid

An amino acid is added to dissolve and stabilize zinc in the treatment solution. The preferred amino acid is glycine ($C_2H_5NO_2$), although other water soluble amino acids are also suitable.

Source of Alkalinity

A source of alkalinity is also provided to help stabilize silicate in the treatment solution. Preferred sources of alkalinity include alkali metal hydroxide bases such as sodium hydroxide or potassium hydroxide. Ammonia or amines may also be used. Suitable exemplary amines include mono-, di-, and triethanolamine, ethylenediamine, diethylenetriamine, triethylenetetramine, tetraethylenepentamine, and polyethylenimine. The use of sources of alkalinity other than ammonia may be advantageous in situations where it is desired to reduce the exposure of personnel to malodorous materials while applying the compositions.

Preparation of Aqueous Preservative Composition

The aqueous preservative compositions of this invention are prepared by dissolving zinc, silicate and boron compounds in aqueous media. An amino acid is included to promote the dissolution of zinc and the solution is adjusted to an alkaline pH to improve the solution stability of zinc and silicate.

In one exemplary method of preparing the preservative compositions of this invention, the amino acid is dissolved in water and the pH is raised by adding an alkali metal hydroxide base, such as sodium hydroxide, before adding the zinc, in order to promote dissolution of the zinc. The solution pH is adjusted to between about 9 and 12.5, preferably about pH 11. The zinc, which optionally may be pre-dissolved in water, is added to this alkaline, amino acid-containing solution before adding the boron and silicate. It is important that the amino acid be added and the pH adjusted before adding the zinc in order to promote effective dissolution of the zinc.

The silicate and boron compounds may each be dissolved separately in aqueous solutions before being added to the zinc solution, but neither one needs to be pre-dissolved. For example, a boron-containing solution may be prepared by dissolving a boron compound, such as TIM-BOR® disodium octaborate tetrahydrate, in water; a silicate solution may be prepared by dispersing N® Clear liquid sodium silicate in water; and a zinc solution may be prepared by dissolving an amino acid in water and adjusting to a solution pH of about 9 to 12.5, preferably about pH 11, with an alkaline base, such as sodium hydroxide, followed by the addition of a soluble zinc salt to the alkaline amino acid-containing solution. The boron and silicate solutions are then added to the zinc solution. Borate is preferably added to the zinc solution before adding the silicate.

Alternatively, the zinc may be added to an aqueous solution of a source of borate containing amino acid in the amounts discussed above, and the silicate solution is then added to this mixture.

It has been found that mere dissolution of zinc borate in ammonia provides preservative compositions with poor borate leach performance; that is, wood treated with such compositions loses borate content when contacted with water over an extended period of time, as measured by test method AWPA E11-97. In contrast, wood that has been treated with compositions prepared according to the invention shows notably lower borate leach rates, and therefore may be expected to retain activity of the preservative for a longer time.

Wood Fibers

Wood fibers according to the invention may be fibers in a piece of wood, or fibers freed from wood by a pulping operation such as is commonly performed in the pulp and paper industry, i.e. wood pulp. As used herein, the term "wood" is to be understood according to its common use, and includes wood pieces or particles of any size or shape, including for example sawn lumber, plywood, oriented strand board, particle board, ground wood, sawdust, and wood/polymer composite materials. The term "wood" according to this use therefore refers to wood that has not been subjected to a pulping operation.

As used herein, the term "wood pulp" refers to wood that has been subjected to a pulping operation, including but not limited to Kraft pulping, sulfite pulping, and chemi-thermo-mechanical pulping. Wood pulp treated according to the invention may be in any form, including but not limited to unconsolidated (loose) pulp fibers, including for example blown insulation, and paper. Paper that comprises wood pulp treated according to the invention may be paper in any form, including but not limited to sheet paper, corrugated board, and paper comprising a surface of gypsum wallboard.

Application of the Preservative Composition

The preservative composition may be applied to the item to be treated by any commercially acceptable method, as long as sufficient composition penetrates into the item so as to result in the deposition of a bioeffective or fire retardant amount of a residual component. It should be noted that the residual component, which is the material that is active for deterrence of biological attack or attack by fire, may comprise zinc, boron, and/or silicon in the form of the compounds that were used to prepare the compositions. They may however represent the result of subsequent chemical reactions in the treated substrate. One possible nonlimiting example is formation of zinc borate in the treated article, but other chemical reactions may occur in addition or instead, or none may occur at all. Similarly, the amino acid may be chemically bound in the treated item, or it may be essentially absent due to other chemical reactions, leaching, or to volatilization out of the item. Regardless of the exact form and location of the zinc, boron, amino acid, and silicon after the treatment is complete, there remains a residual component that provides the preservative properties of the invention. Resistance to insects, wood-decay fungi, and/or fire is thereby achieved.

For wood products, application of the preservative composition may involve a method such as vacuum and/or pressure treatment or dip treatment under atmospheric pressure. Preferably, treatment may involve both vacuum and pressure, wherein a vacuum is first applied to the wood product, prior to application of the aqueous preservative composition. The solution is then applied to the wood product and pressure is then applied to force the solution into the pores of the wood. Preferably, after the wood product has been treated, the treated wood may be dried to improve the leach resistant properties of the wood. Drying may be performed at an elevated temperature, preferably no higher than 90° C., even more preferably no higher than 70° C., with about 60° C. being typical. It has been found that the use of lower drying temperatures for a given amount of drying time tends to reduce the borate leach rate of items treated with these compositions. Thus in some embodiments of the invention, drying is performed under ambient temperatures, typically between about 20° C. and 25° C., optionally aided by the use of vacuum or blown air. Methods for drying wood, and the desired moisture level of dried wood, are well known in the art.

For applications in which resistance to biological attack is the desired result, it is believed that the amount of borate in the treated substrate should be at least 0.1%, measured as boric acid equivalents (BAE). A level of at least 0.5% will typically be used. In general, increased BAE provides increased resistance to biological activity, as well as to fire. Methods for applying the compositions include spraying, roll coating, dipping, and any other means known in the art relevant to the particular form of the wood or wood pulp.

EXAMPLES

Example 1

The following example illustrates a preferred method for preparing the aqueous preservative solution according to the invention. Composition 1 was prepared as follows:

Glycine (14.92 g) was stirred into 126.6 g of deionized water. A 40.0-gram portion of NaOH pellets was stirred into the glycine solution until the NaOH was completely dissolved. Zinc chloride (2.5 g $ZnCl_2$) was added and the mixture was stirred until the zinc chloride was completely dissolved.

In a separate container, 3.0 g of TIM-BOR® disodium octaborate tetrahydrate (manufactured by U.S. Borax Inc.) was dissolved in 126.6 g of deionized water. The TIM-BOR® solution was stirred into the zinc solution.

In a separate container, 7.0 g of N-Silicate® (manufactured by PQ Corporation) was added to 126.6 g of deionized water and stirred until the silicate was completely dispersed. The silicate solution was stirred into the zinc solution.

The resulting solution had a zinc to boron (Zn:B) mole ratio of about 0.32:1, a glycine to zinc mole ratio of about 10.8:1 and a silicon to boron (Si:B) mole ratio of about 0.58:1, and had the following composition:

Composition 1

3.63% glycine
0.29% Zn (0.61% $ZnCl_2$)
0.15% B (0.73% TIM-BOR®)
0.49% $SiO_2$ (1.71% N-Silicate®)

Compositions 2 and 3 were prepared using the same procedures and ratios of ingredients as for Composition 1, but the overall concentrations were as follows:

Composition 2

3.73% glycine
0.30% Zn (0.63% $ZnCl_2$)
0.16% B (0.75% TIM-BOR®)
0.50% $SiO_2$ (1.75% N-Silicate®)

Composition 3

9.45% glycine
0.76% Zn (1.57% $ZnCl_2$)
0.39% B (1.87% TIM-BOR®)
1.29% $SiO_2$ (4.5% N-Silicate®)

Cube-shaped wood blocks measuring 1.9 cm on each side and weighing between 3 and 5 g (20-30 g total) each were vacuum-impregnated with one of aqueous preservative compositions 1, 2, or 3, using AWPA Method E11-97, "Standard Method of Determining the Leachability of Wood Preservatives." The blocks were then dried overnight at 60° C., and evaluated for degree of borate leaching according to Method E11-97. The results of the leaching experiments are shown in Table I, indicating results for a 14-day leach test.

TABLE I

| | Leach Results | | | | | |
|---|---|---|---|---|---|---|
| | Mole Ratio | | | Boron Loading in | Boron Retention | % Boron |
| Composition | Zn:B | N:Zn | Si:B | Wood, % BAE[a] | in Wood, % BAE[a] | Retention |
| 1 | 0.3151 | 10.84 | 0.58 | 1.32 | 0.298 | 22.5 |
| 2 | 0.3145 | 10.83 | 0.57 | 1.07 | 0.298 | 27.8 |
| 3 | 0.3178 | 10.90 | 0.59 | 3.45 | 0.856 | 24.8 |

[a]BAE = Boric Acid Equivalent

As illustrated by the results in Table I, the treatment solutions provided for immobilization of between about 22 and 28% of the boron originally applied to the wood.

The preservative solutions of this invention are suitable for treating wood products to provide leach-resistant protection against biological attack from a variety of wood-destroying organisms, including insects and fungal decay. The compositions may be used alone, or they may be combined with other constituents or other compositions. Various changes and modifications of the invention can be made and to the extent that such changes and modifications incorporate the spirit of this invention, they are intended to be included within the scope of the appended claims.

What is claimed is:

1. An aqueous preservative composition comprising a source of zinc selected from the group consisting of zinc oxide and soluble zinc salts; a source of borate selected from the group consisting of zinc borate, boric acid, boric oxide and water soluble borate salts; an amino acid; an alkali metal silicate; a source of alkalinity; and water; wherein the composition comprises at least 50 wt % water.

2. The preservative composition according to claim 1, wherein the composition is essentially chloride ion free.

3. The preservative composition according to claim 1, wherein the composition is essentially copper-free.

4. The preservative composition according to claim 1, wherein the amino acid is glycine, the source of zinc is zinc chloride, the source of borate is sodium borate, and the alkali metal silicate is sodium silicate.

5. The preservative composition according to claim 1, wherein the source of borate is disodium octaborate tetrahydrate and the alkali metal silicate is sodium silicate having an $SiO_2:Na_2O$ weight ratio greater than 3:1.

6. The preservative composition according to claim 1, wherein the aqueous preservative composition comprises from about 0.1 to about 1.0 weight percent boron, from about 0.2 to about 2.5 weight percent zinc, from about 1 to about 5 weight percent amino acid, and between about 0.1 and about 1 wt % $SiO_2$.

7. The preservative composition according to claim 1, wherein zinc and boron are present in the aqueous preservative composition in a mole ratio Zn:B between about 0.4:1 and 5:1.

8. The preservative composition according to claim 1, wherein zinc and boron are present in the aqueous preservative composition in a mole ratio Zn:B between about 1:1 and 3:1.

9. The preservative composition according to claim 1, wherein zinc and boron are present in the aqueous preservative composition in a mole ratio Zn:B between about 1.5:1 and 2:1.

10. The preservative composition according to claim 1, wherein amino acid and zinc are present in the aqueous preservative composition in a mole ratio amino acid:Zn between about 7:1 and 33:1.

11. An aqueous preservative composition consisting essentially of a source of zinc selected from the group consisting of zinc oxide and soluble zinc salts; a source of borate selected from the group consisting of zinc borate, boric acid, boric oxide and water soluble borate salts; an amino acid; an alkali metal silicate; a source of alkalinity; and water; wherein the composition comprises at least 50 wt % water.

12. The composition according to claim 11, wherein the composition is essentially copper-free.

13. A method of making an aqueous preservative composition, the method comprising the steps of: (a) dissolving a source of zinc in an aqueous amino acid-containing solution comprising a source of alkalinity to produce an aqueous zinc solution; (b) adding to the aqueous zinc solution a source of borate selected from the group consisting of zinc borate, boric acid, boric oxide and water soluble borate salts; (c) mixing until essentially all solids are dissolved; and (d) adding to the mixture produced in step (c) an alkali metal silicate.

14. The method according to claim 13, wherein the composition is essentially copper-free.

15. The method according to claim 13, further comprising, prior to the step of adding the source of borate to the aqueous zinc solution, dissolving the source of borate in water.

16. A method for preserving an article comprising wood fibers, the method comprising the steps of:
(a) applying to the article an aqueous preservative composition prepared by combining ingredients comprising:
    i) a source of zinc selected from the group consisting of zinc oxide and soluble zinc salts;
    ii) a source of borate selected from the group consisting of zinc borate, boric acid, boric oxide and water soluble borate salts;
    iii) an amino acid;
    iv) a source of alkalinity;
    v) an alkali metal silicate; and
    vi) water
such that the aqueous preservative composition penetrates into the wood fibers, wherein the composition is essentially copper-free and comprises at least 50 wt % of water; and
(b) drying the wood fibers;
such that there is deposited therein a bioeffective amount of a residual component comprising zinc, boron, and silicon.

17. The method of claim 16, wherein the composition is essentially copper-free.

18. The method of claim 16, wherein the bioeffective amount of the residual component is sufficient to deter attack on the article by termites.

19. The method of claim 16, wherein the bioeffective amount of the residual component is sufficient to deter attack on the article by wood-decay fungi.

20. The method of claim 16, wherein the drying step is performed at a temperature no higher than 90° C.

21. The method of claim 16, wherein the drying step is performed at a temperature between about 50° C. and about 70° C.

22. The method of claim 16, wherein the drying step is performed at ambient temperature.

23. The method of claim 16, wherein the article comprises wood.

24. The method of claim 16, wherein the article comprises wood pulp.

25. The method of claim 24, wherein the wood pulp is in the form of paper.

26. The method according to claim 23, wherein step (a) involves dip treating the article under atmospheric pressure.

27. The method according to claim 23, wherein step (a) involves application of one or both of vacuum and pressure to facilitate said penetration of the aqueous preservative composition.

28. An article comprising wood fibers comprising a residual component comprising zinc, boron, and silicon, prepared by treating the wood fibers according to the method of claim 16.

29. A method of treating a substrate comprising wood fibers to provide resistance to flame spread, the method comprising the steps of:
(a) applying to the article an aqueous preservative composition prepared by combining ingredients comprising:
    i) a source of zinc selected from the group consisting of zinc oxide and soluble zinc salts;
    ii) a source of borate selected from the group consisting of zinc borate, boric acid, boric oxide and water soluble borate salts;
    iii) an amino acid;
    iv) a source of alkalinity;
    v) an alkali metal silicate; and
    vi) water
such that the aqueous preservative composition penetrates into the wood fibers, wherein the composition comprises at least 50 wt % of water; and
(b) drying the wood fibers;
such that there is deposited therein a flame retardant amount of a residual component comprising zinc, boron, and silicon.

30. The method of claim 29, wherein the composition is essentially copper-free.

* * * * *